(12) United States Patent
Tracy et al.

(10) Patent No.: US 7,088,445 B2
(45) Date of Patent: Aug. 8, 2006

(54) LIGHT SOURCE

(75) Inventors: David H. Tracy, Norwalk, CT (US); Bernhard H. Radziuk, Frickingen (DE); Klaus Fischer, Friedrichshafen (DE)

(73) Assignee: Berthold GmbH & Co. KG (DE)

( * ) Notice: Subject to any disclaimer, the term of this patent is extended or adjusted under 35 U.S.C. 154(b) by 237 days.

(21) Appl. No.: 10/241,863

(22) Filed: Sep. 12, 2002

(65) Prior Publication Data

US 2003/0151740 A1  Aug. 14, 2003

(30) Foreign Application Priority Data

Sep. 13, 2001  (DE) ................ 101 45 172

(51) Int. Cl.
*G01J 3/00*  (2006.01)

(52) U.S. Cl. .................................................. 356/300

(58) Field of Classification Search ........ 356/300–334; 362/224, 225, 227–252
See application file for complete search history.

(56) References Cited

U.S. PATENT DOCUMENTS

| 3,600,571 | A |  | 8/1971 | Chisholm et al. |
|---|---|---|---|---|
| 5,135,305 | A | * | 8/1992 | Fitz-Patrick ................. 356/311 |
| 6,236,457 | B1 | * | 5/2001 | Allen et al. .................. 356/328 |
| 6,377,899 | B1 | * | 4/2002 | Sakai et al. .................. 356/319 |

FOREIGN PATENT DOCUMENTS

| DE | 3602139 A1 | * | 7/1987 |
|---|---|---|---|
| DE | 3723032 |  | 7/1987 |
| DE | 9406263.3 |  | 6/1994 |
| EP | 0 423 736 |  | 10/1990 |

* cited by examiner

*Primary Examiner*—Layla G. Lauchman
(74) *Attorney, Agent, or Firm*—St. Onge Steward Johnston & Reens LLC

(57) ABSTRACT

A light source for an atomizing device, specifically an atom absorption spectrometer comprising one, two, or more lamps, whose ray can be selected by means of at least one two-dimensionally moveable optical selection element, and which can be directed in the direction of atomizing device. Fine-tuning is thereby achieved quickly with little constructive expenditure and with low costs. A very high degree of accuracy is possible from the selector through a rotational and highly adjustable rotation spindle.

11 Claims, 1 Drawing Sheet

LIGHT SOURCE

This application claims priority of pending German Patent Application No. 101 45 172.5 filed Sep. 13, 2001.

FIELD OF THE INVENTION

The invention comprises a light source for an atomizing device, more specifically an atom absorbing spectrometer with one, two or more lamps, the ray from which may be selected by means of an optical selector moveable in at least two dimensions and moveable in the direction of the atomizing device.

Generally, with such aforementioned light sources with atom-absorbing spectrometers, each of the lamps generates an individual spectral line from an element-specific source, which is isolated through a monochromator. In order to carry out an automatic sequential analysis, such an atom-absorbing spectrometer comprises two, three or more lamps, where the light ray is supplied by means of a specific lamp, which selects the atomizing device. Such an atomizing device is usually a flame, a furnace or similar.

BACKGROUND OF THE INVENTION

A known example for a corresponding selection device is the rotational circular transporter, on which the different lamps are arranged and then turned to the corresponding position for the emission of the light radiation in the direction of the atomizing device.

Furthermore, in practice the usual arrangement is known, in which at least one optical element is moved, in order to select a particular lamp of the light source. Such an arrangement has the advantage that automatic fine-tuning can be achieved without moving the lamp itself. For this reason, selection is constructively easier and also much quicker. With such a structure, several measurements can be carried out successively during the atomizing of specific tests with different lamps.

The movement of the optical selector in the above-mentioned device occurs in two dimensions for the lamp selection and for accuracy. Another disadvantage of this device is that it is relatively large and the device controlling two-dimensional movement of the optical element is relatively complex.

SUMMARY OF THE INVENTION

The present invention relates to a light source for an atomizing device the aim of which is to improve and to enable rapid fine-tuning, with little expenditure in construction and with little cost, as well as with a very high degree of accuracy.

The present invention achieves these features as the selector can be rotated and highly fine-tuned by means of a rotating spindle.

In one aspect of the present invention, the selector of a specific lamp of the light source can be aligned through corresponding rotation of the rotating spindle. In another aspect of the present invention, alignment can be achieved in the direction of rotation as well as vertically to the direction of rotation i.e. in the direction of axial rotation of the rotating spindle in an accurate and rapid manner. The mechanism of movement and alignment of the selector is thereby simple and cost-effective. At the same time, the selector can also be adjusted by selection of the thread of the rotating spindle in the direction of rotation as well as in the direction of axial rotation with a higher degree of accuracy and very fine-tuning especially in the direction of axial rotation.

The essence of the invention is therefore not only that two-dimensional movement and alignment of the optical selector is possible, but also that the selector can be turned in three directions.

In order to ensure a compact light source, the lamps can be arranged in a similar fashion with the selector.

In order to render the light source even more compact at least one optical steering element can be situated between the ray outlet slots of each lamp and selector.

In the simplest cases, such a steering element can be a 90°-angle element, through which the light ray of each lamp is bent to 90° in the direction of the selection element.

In order to simplify the arrangement of the selector for each lamp, the lamps can be arranged opposite one another in pairs in relation to the selector. Alternatively, the lamps can be arranged around a centrally situated selector linked not only to the selector, but also to one another.

In order to be able to direct the light ray of each lamp in the direction of the atomizing device and not be hindered by these lamps in one aspect of the present invention, the receiving light ray can be directed by the selector from the specific steering element at 90° to the direction of axial rotation of the rotating spindle. In yet another aspect of the present invention, the corresponding longitudinal axis of the lamps could also be aligned parallel to the direction of axial rotation.

In order to adequately focus the light ray steered by the selector in the direction of the atomizing device, an optical lens or similar device can be placed next to the selector. In an additional, simply constructed arrangement, an optical steering element can be placed in the ray path of the light source next to the selector, which steers the light ray at 90° to the direction of the atomizing device. The steering already ensues in the area of the lamps, the central steering element can be aligned between the lamps, and the ray steered between two adjacent lamps.

The different optical elements to achieve bending of the light ray can in one aspect be built up through prisms or the like. In one aspect of the present invention, selectors and/or steering elements and/or central steering elements can be built with optical reflector elements, such as mirrors or the like.

In another aspect of the present invention, it is possible to operate the rotation spindle for three-dimensional adjustment of the selector by hand. However, if the movement needs to be automated, the rotation spindle can be linked to a drive motor.

In this context, in order to control the rotation of the rotating spindle exactly and automatically, a stepping motor can be used as a drive motor.

Due to its construction and the arrangement of the various optical elements, the light source of the invention is also suitable for lamps with larger bores, such as hollow cathode lamps or electrode free discharge lamps.

DETAILED DESCRIPTION OF THE DRAWINGS

Figure 1:
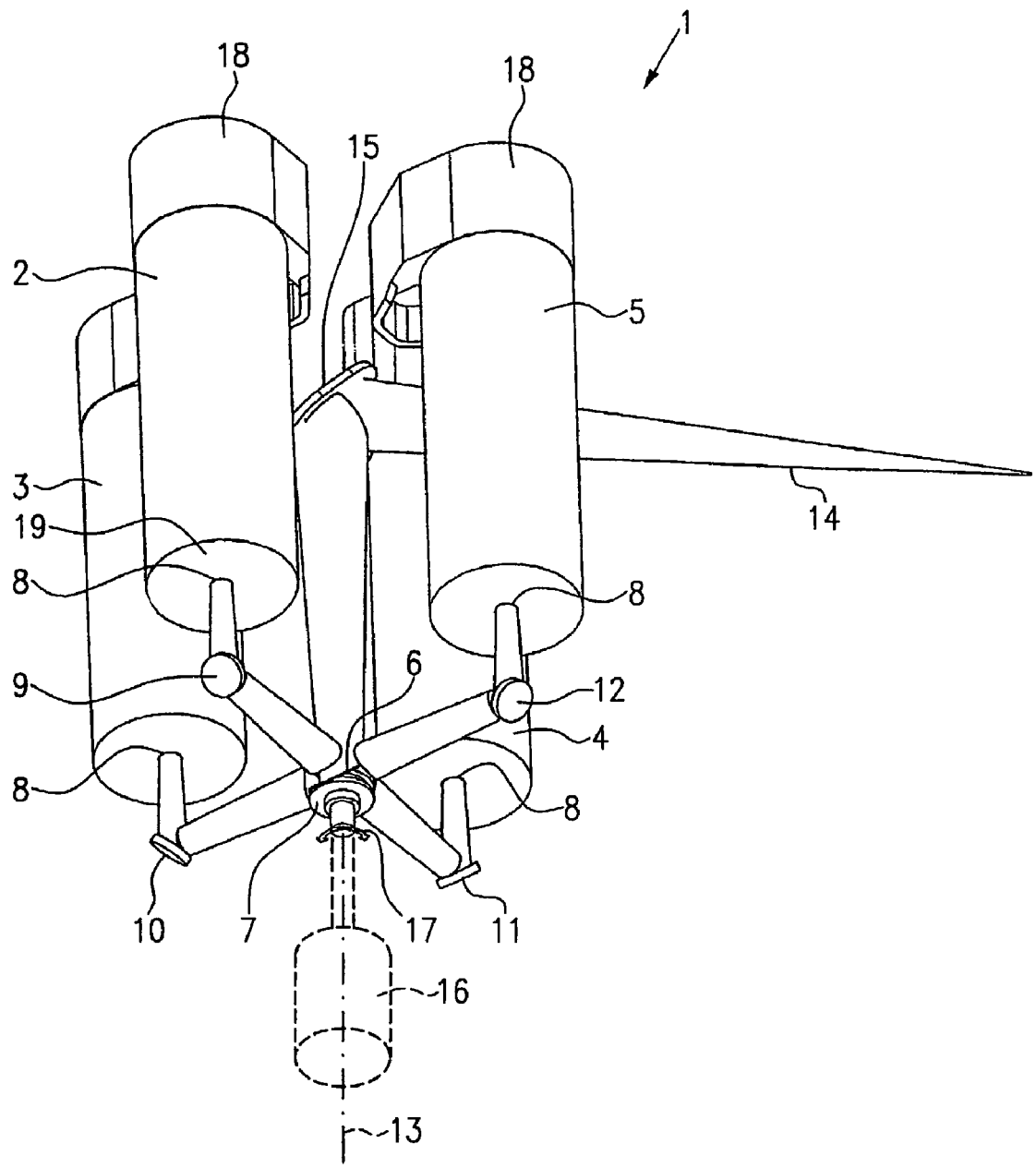
FIG. 1 is a perspective view from diagonally below the light source of the present invention.

In FIG. 1 a view is portrayed from a perspective diagonally below the light source 1 of the present invention.

Altogether, the light source comprises lamps 2, 3, 4 and 5, which are arranged diametrically opposite to each other on a central axis or along the direction of axial rotation 13. Lamps 2, 3, 4 and 5 are secured by means of lamp supports or fittings 18, for example plugs and lamps, such as hollow cathode lamps or electrode free discharge lamps. Light can be supplied by means of these lamps, which corresponds to the individual spectral line from an element-specific source. The light is produced by an atomizing device of an atom absorption meter (not shown) and serves as proof of a specific atomized element in the atomizer device.

Lamps 2, 3, 4 and 5 comprise lamp supports 18 opposite each other with the lower ends 19 comprising radiation outlet windows 8. The light ray passes through this in the direction of one of the optical steering elements 9, 10, 11 and 12 set up for each lamp. This steering element can bend the ray at 90° to the direction of the rotational axis 13.

A rotating spindle 7 is set up in the direction of axial rotation 13. This can be rotated through a drive motor 16 used specifically as stepping motor, which can be turned to the direction of rotation 17. An optical selector 6 aligned by this can be rotated in linear by using the rotating spindle 7 to the direction of rotation 17 and to the direction of axial rotation 13. Selector 6 is aligned between steering elements 9, 10, 11, and 12. By means of the selector 6 a ray is supplied by steering elements 9, 10, 11 and 12 at an angle of 90° to the direction of axial rotation.

A central steering element 15 is aligned between lamps 2, 3, 4 and 5, through which the ray from the selected lamp 2, 3, 4 and 5 is bent by the relevant steering element 9, 10, 11 12 and the selector 6 at an angle of 90° to the direction of the atomizing device. A ray path 14 passes through this arrangement of steering elements 9, 10, 11 and 12, selector 6 and central steering element 15, as shown in FIG. 1. With the position of the selection element 6 as portrayed in FIG. 1, the light ray is emitted from lamp 2 of the atomizing device. The light ray is therefore discharged between adjacent lamps 4 and 5 from lamp 2 by means of the central steering element 15.

In the embodiment depicted in FIG. 1, the various optical elements i.e. steering elements 9, 10, 11 and 12 and selector 6 are fashioned as flat and level mirror surfaces. The central steering element 15 is an elliptical mirror.

It should be noted that the ray path can also run in this way, for example the light ray leaves the light source 1 along the direction of axial rotation 13. In this case, a reflecting central steering element is not needed and, if necessary, a focusing optical element may be used instead or integrated in selection element 6.

Hereafter, the functions portrayed in the example in FIG. 1 of the invention are explained in short.

The various lamps 2, 3, 4 and 5 of the light source can all be operated simultaneously. The choice of a specific lamp and therewith a specific spectral line for the ray of one probe contained in the atomizing takes place by means of the corresponding rotation of the selector 6 by means of the rotation spindle 7. This is also served by the stepping motor 16. The selector 6 is positioned and orientated accurately by rotation to the direction of rotation 17, as well as to the direction of rotation 13, so that the light ray of lamp 2 is controlled and carried out by steering element 9, selector 6 and central steering element 15 of the atomizing device. Along with the rotation spindle 17 with selector 6 included, the remaining components of the light source 1 are fixed, so that no more parts must be moved or aligned. This results in an especially compact arrangement of all components with the simultaneously simplified and quicker choice of light of a specific lamp.

The invention claimed is:

1. Light source for an atomizing device with one, two or several lamps, the ray of which may be selected by means of at least one optical selector, the at least one optical selector moveable at least in the direction of the atomizing device characterized by the fact that a selector can be turned by means of a rotational spindle, and between radiation outlet windows of each lamp and selector, an at least one optical steering element is arranged.

2. Light source mentioned in claim 1, characterized by the fact that lamps are essentially linked to the selector and are arranged in a similar fashion to the selector.

3. Light source mentioned in claim 1, characterized by the fact that the steering element is a 90° steering element.

4. Light source mentioned in claim 1, characterized by the fact that the lamps are aligned in pairs diametrically facing each other in relation to the selector.

5. Light source mentioned in claim 1, characterized by the fact that, through the selector which can steer the ray received from the light source by means of the steering elements, the rotation spindle can be steered to the direction of axial rotation.

6. Light source mentioned in claim 1, characterized by the fact that the ray path of the light source is arranged subsequent to the selector and the optical central steering element, which the radiation essentially at 90° turns to the direction of atomizing device.

7. Light source mentioned in claim 1, characterized by the fact that a central steering element is arranged between the lamps to steer the ray between two adjacent lamps.

8. Light source mentioned in claim 1, characterized by the fact that an element selected from the group comprising a selector, a steering element, a central steering element, and combinations thereof is supplied as optical reflection elements.

9. Light source mentioned in claim 1, characterized by the fact that the rotation spindle is linked to a drive motor.

10. Light source mentioned in claim 1, characterized by the fact that a drive motor is provided as a stepping motor.

11. Light source mentioned in claim 1, characterized by the fact that the lamp is a hollow cathode lamp or electrode free discharge lamp.

* * * * *